United States Patent [19]

Arkans

[11] 4,152,748
[45] May 1, 1979

[54] MULTIPLE TRANSDUCER

[76] Inventor: Edward J. Arkans, 1300 E. Algonquin Rd., Schaumburg, Ill. 60195

[21] Appl. No.: 794,294

[22] Filed: May 5, 1977

[51] Int. Cl.² .............................................. H01G 7/00
[52] U.S. Cl. ....................................... 361/283; 73/379; 73/782; 73/779; 361/278; 361/330
[58] Field of Search ...................... 73/718, 724, 304 C, 73/379; 361/290, 275, 283, 330, 288, 278; 324/61 P; 128/2 R, 2 S

[56] References Cited

U.S. PATENT DOCUMENTS

| 942,620 | 12/1909 | Dearlove | 361/330 X |
|---|---|---|---|
| 1,255,597 | 2/1918 | Giles | 361/275 |
| 2,290,387 | 7/1942 | Schwartz | 128/2 S |
| 2,755,796 | 7/1956 | Boucke | 128/2 R |
| 2,866,141 | 12/1958 | Frank | 361/283 |
| 3,177,967 | 4/1965 | Wilson | 361/283 |
| 3,225,274 | 12/1965 | Herr | 361/283 |
| 3,230,431 | 1/1966 | Deniston | 361/290 X |
| 3,678,378 | 7/1972 | Trott | 361/283 X |
| 3,898,983 | 8/1975 | Elam | 128/2 S |
| 3,965,399 | 6/1976 | Walker | 361/288 |
| 3,974,491 | 8/1976 | Sipe | 128/2 S |

FOREIGN PATENT DOCUMENTS

| 425745 | 3/1935 | United Kingdom | 361/330 |
|---|---|---|---|
| 752699 | 7/1956 | United Kingdom | 73/304 C |

OTHER PUBLICATIONS

Levine, Try Capacitance Transducers in Electrical Design, 3/66, p. 188 only.

Primary Examiner—E. A. Goldberg
Attorney, Agent, or Firm—Powell L. Sprunger

[57] ABSTRACT

A transducer system comprising, a multiple capacitive transducer having a flexible dielectric sheet of elastic nonconductive material, a first plate of flexible conductive material defining a region located adjacent a first surface of the sheet, and a plurality of second plates of flexible conductive material located adjacent a second surface of the sheet, with the second plates defining areas aligned with the region of the first plate. The system separately forms signals responsive to the capacitance between the first and second plates.

11 Claims, 8 Drawing Figures

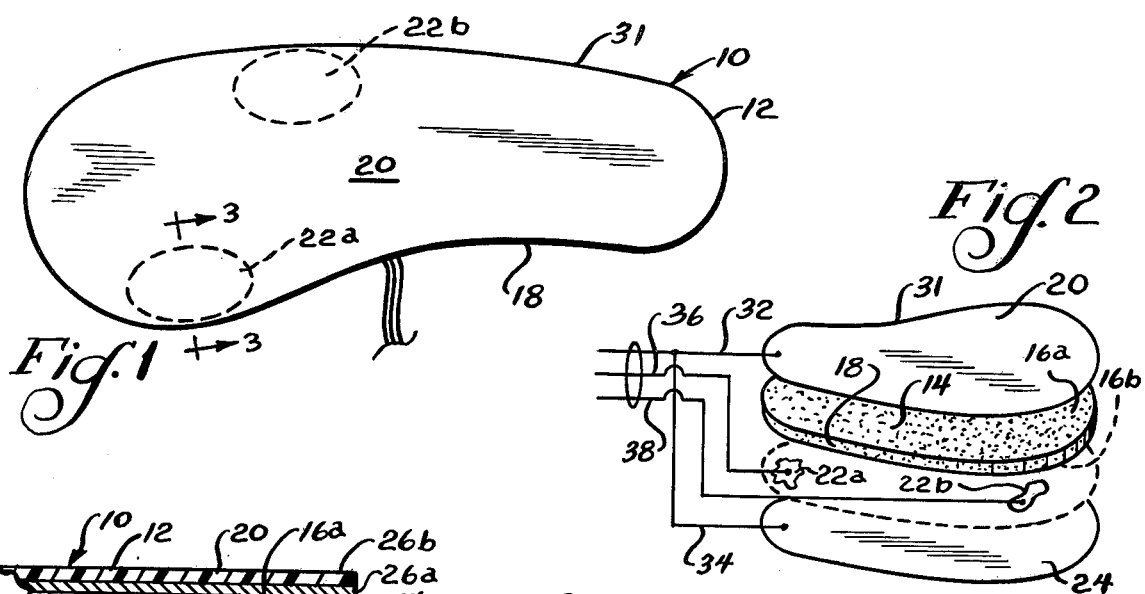
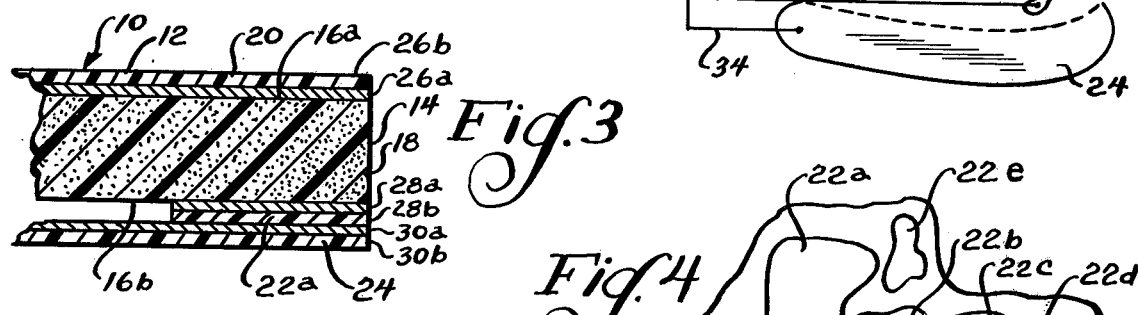
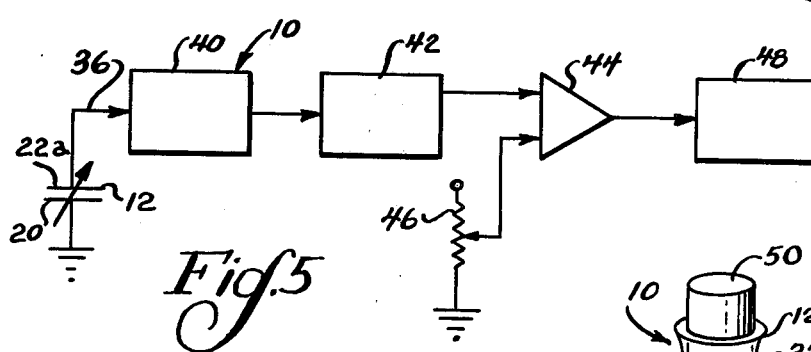
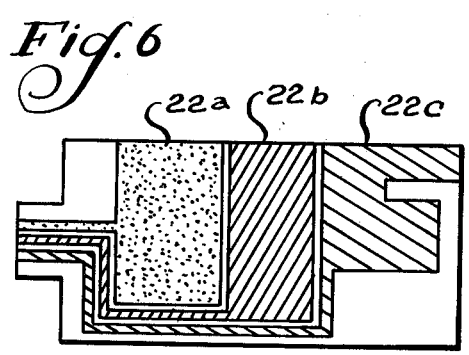
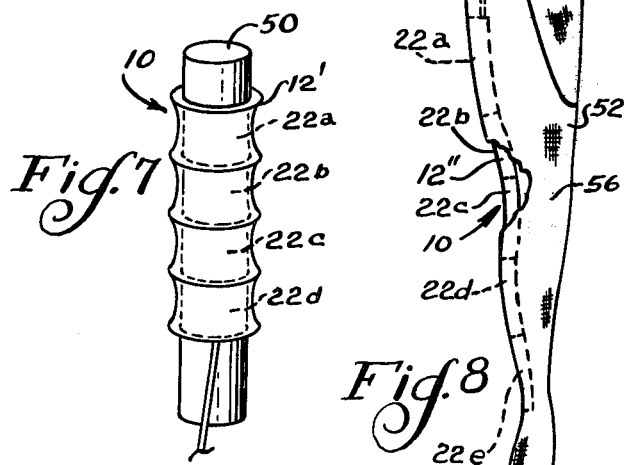

MULTIPLE TRANSDUCER

BACKGROUND OF THE INVENTION

The present invention relates to transducers, and more particularly to transducers for measuring forces in a plurality of areas.

A number of patients suffer from lower limb injuries, such as ulcerations of the plantar surface of the foot, collapse of the metatarsal arch, bone spurs of the plantar surface joints, heel spurs, and other pathologies contributing to abnormal gait. Further, diabetic patients may experience ulcerations of the skin attributable to relatively poor peripheral circulation, and other patients may experience anesthesia of the limbs.

Conventionally, treatment of the above problems has often included the fitment of a shoe orthosis in order to redistribute weight toward the unaffected areas of the sole. The design of such a orthosis has been based upon X-rays, visual examination of the plantar surface, observations of gait, and identification of painful areas by the patient. Normally, the patient wears the orthosis over a period of time, and returns to the physician when he undergoes an examination to assess his progress. Frequently, the orthosis is altered in order to provide a better redistribution of weight.

Although observation of the patient's gait may provide some information about conditions of the plantar surface, the current practice is rather subjective in nature, and the detection of gait abnormalities and consequent approach to treatment has been met with varied and inconsistent results.

SUMMARY OF THE INVENTION

A principal feature of the present invention is the provision of a multiple transducer system of simplified construction for determining forces in an improved manner.

The transducer system of the present invention comprises, multiple capacitive transducer means comprising, flexibile dielectric sheet means of elastic nonconductive material having a pair of opposed first and second surfaces. The transducer means has a first plate of flexible conductive material defining a region located adjacent the first surface of the sheet means has a first plate of and a plurality of second plates of flexible connductive material located adjacent the second surface of the sheet means, with the second plates defining areas aligned with the region of the first plate. The system has means for separately forming signals responsive to the capacitance between the first and second plates.

A feature of the present invention is that the system separately determines the forces applied against the transducer means in the areas defined by the second plates.

Another feature of the present invention is that the measuring areas defined by the second plates may be formed in arbitrary configurations, and may be overlapped.

Yet another feature of the invention is that the plates may be constructed from a flexible plastic-coated conductive foil, and the sheet means may be constructed from a nonconductive foam.

Thus, a feature of the invention is that the transducer means may be formed in a simplified manner and at a reduced cost.

Still another feature of the invention is that the flexible transducer means conforms to irregular surfaces.

A feature of the invention is that the system may be readily utilized to measure the forces applied by a patient's foot under static and dynamic conditions.

A further feature of the invention is that the system may be utilized to measure the forces exerted by a patient's fingers during rehabilitation of the hand.

Still another feature of the invention is that the system may be utilized to measure the compressive pressures exerted by a stocking during testing.

Further features will become more fully apparent in the following description of the embodiments of this invention and from the appended claims.

DESCRIPTION OF THE DRAWINGS

In the drawings:

FIG. 1 is a top plan view of a transducer element for a system of the present invention illustrated as a sole for a patient's shoe;

FIG. 2 is an exploded diagrammatic view of the system of FIG. 1;

FIG. 3 is a fragmentary sectional view on an enlarged scale taken substantially as indicated along the line 3—3 of FIG. 1;

FIG. 4 is a diagrammatic view illustrating configurations of measuring areas for the transducer system of the present invention;

FIG. 5 is a diagrammatic view of a circuit for the system of the present invention;

FIG. 6 is a diagrammatic view of a plate for the system of the present invention;

FIG. 7 is a perspective view of a transducer element of the present invention for testing the grip of a patient's hand; and FIG. 8 is a perspective view of a transducer element for testing the compressive pressures exerted by a therapeutic stocking.

DESCRIPTION OF THE PREFERRED EMBODIMENTS

Referring now to FIGS. 1-3, there is shown a transducer system generally designated 10 having a transducer element 12 illustrated in the form of a sole for placement in a patient's shoe beneath the patient's foot, although the system 10 of the present invention has many other useful purposes, such as those described below. The transducer element 12 has a flexible dielectric sheet 14 of elastic nonconductive material, such as neoprene foam, having a pair of opposed first and second surfaces 16a and 16b, respectively, and side edges 18 bounding a region of the sheet 14 generally in the shape of the patient's foot. The element 12 has a first plate 20 of conductive material defining a region located adjacent the first surface 16a of the sheet 14, a plurality of second plates 22a and 22b of conductive material located adjacent the second surface 16b of the sheet 14, and a third plate 24 of conductive material located adjacent the second surface 16b of the sheet 14 and covering the second plates 22a and b, with the third plate 24 being insulated from the second plated 22a and b.

In a preferred form, the first and third plates 20 and 24 have a configuration approximating the shape of the flexible sheet 14, such that the first and third plates 20 and 24 also conform to the shape of the patient's foot. In a preferred form, the plates may be made from a flexible metallic foil, such as copper, having an insulating coating, such as plastic, on one surface thereof. Thus, the plates may be constructed from a laminate of a suitable plastic and metallic conductive foil, such that the plates and sheet 14 may be readily formed to the desired shape by a suitable cutting instrument, such as scissors.

With reference to FIG. 3, the transducer element 12 has its first plate 20 placed against the first surface 16a of the sheet 14, with the first plate 20 having a conductive layer 26a facing the sheet 14, and an insulating layer 26b facing away from the sheet 14. The second plates 22 are placed against the second surface 16b of the sheet 14, with the second plates having an inner conductive layer 28a facing the sheet 14 and an outer insulating layer 28b facing away from the sheet 14. Similarly, the third plate 24 has an inner conductive layer 30a facing toward the flexible sheet 14, and an outer insulating layer 30b facing away from the sheet 14. The transducer element 12 may be assembled by bonding the plates and flexible sheet together through use of a suitable adhesive. In this configuration, the second plates 22a and b define active measuring areas aligned with the region bounded by edges 31 of the first plate 20, with the transducer system 10 separately determining the capacitance between the first plate 20 and second plates 22a and b and measuring the forces applied against the transducer element 12 in the areas defined by the second plates 22a and b.

It will be apparent that the third plate 24 has a fixed position relative the second plates 22a and b, but the spacing between the first plate 20 and second plates 22a and b becomes reduced responsive to application of force in the areas of the second plates due to the elasticity and resiliency of the sheet 14. Accordingly, the pressure P applied to the transducer element 12 causes a reduction of distance $\Delta d$ between the first plate 20 and second plates 22a and b according to the relationship $P = Y \Delta d$, where Y is Young's Modulus. The change of capacitance $\Delta C$ responsive to application of force and change of distance $\Delta d$ between the first plate 20 and separate second plates 22a and b is defined by the equation, $$\Delta C = \epsilon_o \epsilon A / \Delta d,$$

where
$\epsilon_o$ is the electrical permitivity in a vacuum,
$\epsilon$ is the dielectric constant, and
A is the area of the given second plate.
It will be seen that the above equations result in the relationship of $$\Delta C = \epsilon_o \epsilon A Y /, P$$

since $P = F/A$,
where F is the applied force. Thus, it is apparent that $$\Delta C 32 \epsilon_o \epsilon A^2 Y / F,$$

and, since the numerator on the right side of this equation contains known constants, the relationship reduces to the form of $$C = k (1), /F,$$

illustrating that a change or difference in capacitance responsive to applied force is inversely proportional to the force. Accordingly, the capacitance between the second plates 22a and b and the first plate 20 may be separately measured in order to determine a change of capacitance which is indicative of the magnitude of the applied forces in an inverse manner.

With reference to FIG. 2, the first plate 20 is connected to an electrical conductor or line 32, and the third plate 24 is connected to an electrical conductor or line 34 which in turn is connected to the line 32. As shown, the second plate 22a is connected to a conductor or line 36, while the second plate 22b is connected to a conductor or line 38. In a preferred form, the lines 32 and 34 are connected to ground, such that the first and third plates 20 and 24 shield the second plates 22a and b in order to minimize effects by a patient relative to his capacitance to ground. In addition, it is preferred to shield the lines 36 and 38 in order to minimize the capacitive effects on these conductors.

A circuit is illustrated in FIG. 5 for the transducer element 12, with a separate circuit of this type being provided for each of the lines from the active second plates, such as the plate 22a defining a variable capacitor in conjunction with the first plate 20 for measuring a difference of capacitance responsive to forces applied in the area of the second plate 22a. In a suitable form, as shown, the plates 20 and 22a of transducer element 12 may be connected as a variable capacitor in an astable multi-vibrator circuit 40 having a square wave output signal connected to the input of a phase-locked-loop circuit 42. The multi-vibrator circuit 40 incorporates the capacitance of the transducer 12 in order to determine the astable frequency, and modifies the frequency of the square wave output signal responsive to a change of measured capacitance of the transducer element 12, with the frequency of the output signal being inversely proportional to the measured capacitance of the transducer element 12. A suitable integrated circuit may be utilized for the astable multi-vibrator circuit 40, such as a 555 timer sold by Signetics Corporation of Sunnyvale, Calif.

The phase-locked-loop circuit 42 serves to demodulate the input frequency into a DC voltage as its output signal which is connected to the input of a suitable amplifier 44. The phase-locked-loop circuit 42 compares the frequency of the input square wave signal to a reference frequency, and forms an output signal for the amplifier 44 which is inversely proportional in magnitude to the frequency of the square wave signal. The phase-locked-loop circuit may be of any suitable type, such as an integrated circuit 565, sold by said Signetics Corporation. The circuit may have a potentimeter 46 of known type in order to define a reference signal for the amplifier 44 which is removed from the output signal of the phase-locked-loop circuit 42. In this manner, a reference voltage level for the amplifier 44 may be suitably adjusted in order to form a desired output signal from the amplifier 44, such as null, when the transducer element 12 is free from loads. In addition, the gain of the amplifier may be adjusted in order to control the magnitude of the output signal per unit of applied force. The output signal from the amplifier 44 may be connected to any suitable device for recording or monitoring the system 10, such as a chart recorder 48.

Thus, when forces are applied against the transducer element 12 and the spacing between the first and second plates 20 and 22a become reduced, the multi-vibrator circuit 40 causes a change of frequency in the corresponding output signal, which in turn results in modifications of the signals from the phase-locked-circuit 42 and the amplifier 44 for controlling the recorder 48. In this manner, the circuit measures the capacitance of the transducer element 12 and forms a signal generally proportional to the forces applied against the transducer element 12. It has been found that the transducer system has excellent linearity from relatively small weights, such as the weight of a coin, to relatively large weights, such as the weight of an adult.

Thus, in accordance with the present invention, the transducer system 10 has a plurality of active measuring areas defined by the configuration of the second plates 22, such that the transducer element measures the applied forces in the separate areas. As shown in FIG. 4, any number of areas may be separately defined by the plates 22 in an irregular configuration. As shown, the areas defined by the plates 22a, 22b, 22c, 22d, and 22e may be spaced or overlapped, as desired. Accordingly, the two plate areas 22a and 22b are overlapped and the three plates 22b, 22c, and 22d are overlaped to define active measuring areas for the transducer system which include regions of intersecton. Further, with reference to FIG. 6, the areas defined by the second plates, such as plates 22a, 22b, and 22c and their leads, may be formed by suitable etching of a conductive plate or by deposition of a conductive material onto a supporting layer.

In use, the transducer element or sole 12 of FIG. 1 may be inserted into a patient's shoe; and the pressure points beneath the patient's foot may be determined by the system while the patient stands or walks. The system 10 thus provides the physician with a basis for determining the amount of pressure which should be relieved in selected areas of the foot, and facilitates the design of therapeutic devices, such as orthopedic shoes. It will be apparent that the transducer element may be readily inserted into the patient's shoe, and the device is nonrestrictive of the patient's foot motion during use.

Another embodiment of the present invention is illustrated in FIG. 7, in which like reference numerals designate like parts. In this embodiment, the transducer system 10 comprises a transducer element 12' having a plurality of active measuring areas defined by second plates 22a, b, c, and d laterally spaced along the transducer element 12'. As shown, the transducer element 12' extends circumferentially around a support member 50, and the second plates 22 are positioned to underlie the patient's fingers during grasping, and may be used to measure improvement of grasping strength during rehabilitation of the patient. The transducer element 12' may have an arrangement of plates and nonconductive sheet as previously described in connection with the transducer element of FIGS. 1-3.

Another embodiment of the present invention is illustrated in FIG. 8, in which like reference numerals designate like parts. In this embodiment, the flexible transducer element 12" may have an elongated configuration for placement intermediate a therapeutic stocking 52 and support member 54, such as a leg form or a wearer's leg. The transducer element 12" has a plurality of longitudinally located second plates 22a, b, c, d, and e which may extend substantially the length of a boot portion 56 of the stocking 52, such that the transducer system 10 may determine the compressive pressures applied by the stocking 52 against the support member 54. As known, such therapeutic stockings preferably apply a graduated pressure against the leg which gradually decreases from the wearer's ankle to the upper part of the thigh, although the pressure profile may be reduced in the region of the knee, if desired. Thus, the transducer system 10 of the present invention may be utilized as a testing device in order to determine whether the therapeutic stocking 52 applies the desired pressures against the support member 54. The transducer element 12" may be constructed from first, second, and third plates and from a nonconductive dielectric sheet, as previously described in connection with the transducer element of FIGS. 1-3.

The foregoing detailed description is given for clearness of understanding only, and no unnecessary limitations should be understood therefrom, as modifications will be obvious to those skilled in the art.

I claim:

1. A transducer system, comprising:
   multiple capacitive transducer means comprising, flexible dielectric sheet means of elastic nonconductive material having a pair of opposed first and second surfaces, a first plate of flexible conductive material defining a region located adjacent the first surface of said sheet means, and a plurality of second plates of flexible conductive material located adjacent the second surface of said sheet means with at least one of said second plates being electrically isolated from another of said second plates, and with said second plates defining areas aligned with said region of the first plate, said first and second plates being spaced from each other by the elastic sheet means, with the spacing between the first and second plates decreasing while the sheet means compresses responsive to application of force against the transducer means;
   means for separately forming signals responsive to the capacitance between said first and each of a plurality of said second plates and for separately measuring the formed signals; and
   an elongated tapered support member simulating the shape of a human leg and adapted to receive a stocking, in which said transducer means extends along a substantial length of the support member, and in which the second plates define longitudinally located regions for measuring the pressures exerted by the placed stocking in said regions against the support member.

2. The system of claim 1 wherein the forming means comprises means for separately forming signals indicating a change of capacitance between the first and second plates responsive to the application of force against the transducer means in the areas of said second plates.

3. The system of claim 1 wherein the forming means comprises means for separately forming signals as a generally linear function of the capacitance between said first and second plates.

4. The system of claim 3 wherein the forming means comprises means for separately forming signals generally proportional to the capacitance between the first and second plates.

5. The system of claim 1 wherein said sheet means comprises a foam material.

6. The system of claim 1 wherein the areas of said second plates are spaced from each other.

7. The system of claim 1 including a third plate covering said second plates and being electrically connected to said first plate, and including insulating means intermediate said second plates and third plate.

8. The system of claim 7 wherein said plates comprise a plastic coated metallic foil, with the foil of said first, second, and third plates facing toward the dielectric sheet means.

9. The system of claim 7 wherein said first and third plates are electrically connected to ground.

10. A transducer system, comprising:

multiple capacitive transducer means comprising, flexible dielectric sheet means of elastic nonconductive material having a pair of opposed first and second surfaces, a first plate of flexible conductive material defining a region located adjacent the first surface of said sheet means, and a plurality of second plates of flexible conductive material located adjacent the second surface of said sheet means with at least one of said second plates being electrically isolated from another of said second plates, and with said second plates defining areas aligned with said region of the first plate, said first and second plates being spaced from each other by the elastic sheet means, with the spacing between the first and second plates decreasing while the sheet means compresses responsive to application of force against the transducer means;

means for separately forming signals responsive to the capacitance between said first and each of a plurality of said second plates and for separately measuring the formed signals; and an elongated generally cylindrical relatively rigid support member being of a shape and size to be grasped around the human hand, in which said transducer means extends at least partially around the support member, and in which said second plates define a plurality of regions disposed along the length of the support member for placement beneath the fingers during grasping of the transducer means.

11. A transducer system, comprising:

multiple capacitive transducer means comprising, flexible dielectric sheet means of elastic nonconductive material having a pair of opposed first and second surfaces, a first plate of flexible conductive material defining a region located adjacent the first surface of said sheet means, and a plurality of second plates of flexible conductive material located adjacent the second surface of said sheet means with at least one of said second plates being electrically isolated from another of said second plates, and with said second plates defining areas aligned with said region of the first plate, said first and second plates being spaced from each other by the elastic sheet means, with the spacing be between the first and second plates decreasing while the sheet means compresses responsive to application of force against the transducer means, with the areas of a plurality of said second plates overlapping in regions, and including insulating means intermediate said second plates in the overlapped regions; and means for separately forming signals responsive to the capacitance between said first and each of a plurality of said second plates and for separately measuring the formed signals.

* * * * *

UNITED STATES PATENT AND TRADEMARK OFFICE
CERTIFICATE OF CORRECTION

PATENT NO. : 4,152,748
DATED : May 1, 1979
INVENTOR(S) : Edward J. Arkans

It is certified that error appears in the above–identified patent and that said Letters Patent are hereby corrected as shown below:

Column 1, line 47, delete "has a first".

Column 1, line 47, after "means" add -- , -- .

Column 1, line 48, delete "plate of".

Column 1, line 48, change "conn-" to -- con- -- .

Column 2, line 61, change "plated" to -- plates -- .

Column 3, line 56, change "$\Delta C$ 32 $\epsilon_o \epsilon A^2 Y/F$," to -- $\Delta C = \dfrac{\epsilon_o \epsilon A^2 Y}{F}$ , --

Column 4, line 48, change "potentimeter" to -- potentiometer -- .

Column 7, line 27, after "around" insert -- by -- .

Column 8, line 18, delete "be".

Signed and Sealed this

Thirty-first Day of July 1979

[SEAL]

Attest:

LUTRELLE F. PARKER

*Attesting Officer*    *Acting Commissioner of Patents and Trademarks*